US012728008B2

(12) United States Patent
Peterson et al.

(10) Patent No.: US 12,728,008 B2
(45) Date of Patent: Sep. 8, 2026

(54) LENGTH-MODULATING TOTAL JOINT PROSTHESIS AND METHOD

(71) Applicants: Melanie Peterson, Potomac, MD (US); Sang-Eun Song, Orlando, FL (US)

(72) Inventors: Melanie Peterson, Potomac, MD (US); Sang-Eun Song, Orlando, FL (US)

(*) Notice: Subject to any disclaimer, the term of this patent is extended or adjusted under 35 U.S.C. 154(b) by 616 days.

(21) Appl. No.: 18/197,629

(22) Filed: May 15, 2023

(65) Prior Publication Data

US 2024/0024116 A1 Jan. 25, 2024

Related U.S. Application Data

(60) Provisional application No. 63/345,342, filed on May 24, 2022.

(51) Int. Cl.
*A61F 2/36* (2006.01)
*A61F 2/30* (2006.01)

(52) U.S. Cl.
CPC ........ *A61F 2/3601* (2013.01); *A61F 2/30734* (2013.01); *A61F 2002/3006* (2013.01); *A61F 2002/30079* (2013.01); *A61F 2002/30153* (2013.01); *A61F 2002/30224* (2013.01); *A61F 2002/30329* (2013.01); *A61F 2002/30405* (2013.01); *A61F 2002/30523* (2013.01); *A61F 2002/3055* (2013.01); *A61F 2002/30593* (2013.01); *A61F 2002/30601* (2013.01); *A61F 2002/30738* (2013.01)

(58) Field of Classification Search
CPC .... A61F 2/3601; A61F 2/3609; A61F 2/3662; A61F 2/367; A61F 2/3672; A61F 2002/3625; A61F 2002/365; A61F 2002/3652; A61F 2002/30329; A61F 2002/30601; A61F 2002/3055; A61F 2002/30706; A61F 2002/30523; A61F 2002/30525; A61F 2250/0007; A61B 17/7216
See application file for complete search history.

(56) References Cited

U.S. PATENT DOCUMENTS

2006/0004459 A1* 1/2006 Hazebrouck .............. A61F 2/36 623/23.45
2006/0030395 A1* 2/2006 Thomas .............. G07F 17/3293 463/17

(Continued)

*Primary Examiner* — Javier G Blanco
(74) *Attorney, Agent, or Firm* — Patent Law Clinic, NYLS

(57) ABSTRACT

A total joint prosthesis that achieves non-invasive length modification and a method of using the same is provided. A gearbox housing within the implant contains a lengthening mechanism comprising a rotatable magnetic rod mechanically coupled to a lengthening screw through a series of parallel gear sets. The lengthening screw is coupled to an internally threaded implant neck. An external magnetic device containing at least one rotatable magnet produces a magnetic field. After total joint arthroplasty, the magnetic field of the external device forces rotation of the internal magnetic rod, causing rotation of the lengthening screw. Rotation of the lengthening screw causes the neck to either compress toward or extend away from the housing, adjusting the overall length of the implant and limb. This invention thus provides non-invasive means for post-operative limb-length modification after total joint arthroplasty and is useful in treating conditions such as limb-length discrepancy.

9 Claims, 18 Drawing Sheets

(56) References Cited

U.S. PATENT DOCUMENTS

| | | | | |
|---|---|---|---|---|
| 2006/0069447 | A1* | 3/2006 | DiSilvestro | A61F 2/38<br>623/23.45 |
| 2012/0209269 | A1* | 8/2012 | Pool | A61B 17/725<br>606/63 |
| 2014/0250674 | A1* | 9/2014 | Pool | A61B 17/68<br>29/525.11 |
| 2016/0262912 | A1* | 9/2016 | Burnikel | A61F 2/4684 |

* cited by examiner

820

LENGTH-MODULATING TOTAL JOINT PROSTHESIS AND METHOD

INCORPORATION BY REFERENCE

This application claims priority to provisional patent application No. 63/345,342, filed May 24, 2022, the contents of which are incorporated herein by reference.

BACKGROUND

I. Field of the Invention

The subject invention relates to a length-modulating medical device surgically implanted to treat a patient's limb length discrepancies.

II. Background of the Invention

Limb Length Discrepancy is an incongruity of limb lengths due to a difference in long bone length or orientation. It is also known as Limb Length Insufficiency or Anisomelia. Approximately 70% of the population may experience some limb-length asymmetry, with clinically significant length defects ranging from 20 to as much as 70 mm. The condition is often caused by trauma-related injuries, abnormal healing of broken bones, or adverse surgical outcome following procedures such as total joint arthroplasty of both the hip and shoulder joints. Congenital deformities, hereditary exostoses, Ollier disease, neurofibromatosis, and other bone infections or diseases can also cause Limb Length Discrepancy.

Leg Length Discrepancy can debilitatingly affect a patient's quality of life and wellbeing. It can cause pelvic obliquity and lateral flexion of the spine, deteriorate femoral head containment and disturb the weight distribution to the hip and knee joints. Limb Length Discrepancy is also associated with an increased likelihood of hip, knee, and lumbar spine osteoarthritis. Other effects include postural scoliosis, stress fractures, wedging of vertebral discs, and bone spurs—all contributing to severe back and joint pain. Muscle spasms, pain, weakness and nerve injury from mechanical stress associated with Limb Length Discrepancy can contribute to an overall loss in mobility and other physiological impairments.

Leg Length Discrepancy is often a consequence of total hip arthroplasty, a common solution to severe osteoarthritis of the acetabulofemoral joint. Over 450,000 individuals undergo total hip arthroplasty per year in the United States. Limb Length Discrepancy has been perceived between 6% and 32% of total hip arthroplasty patients, with average leg length discrepancies ranging from 3 to 17 mm, having a high of 70 mm. The majority of total hip arthroplasty patients suffering from Limb Length Discrepancy experience a longer surgical limb. During total hip arthroplasty, surgeons are expected to determine intraoperatively the precise length of a hip implant that would equalize the leg lengths after surgery. An overall lack of standardization of measuring techniques may exacerbate the risk and persistence of error in sizing length-modular hip implants. If an inappropriate length or implant angle is used, there is no definitive treatment to repair Leg Length Discrepancy without revision surgery granularly. Conservative treatments for Limb Length Discrepancy, such as insoles or orthotics, often cause further biomechanical damage, and revision surgery would cost the patient time, money, pain, discomfort, and quality of life. Neither are an adequate solution to correct Limb Length Discrepancy after total hip arthroplasty.

Intramedullary lengthening nails have been used to elongate long bones like the femur or humerus. However, intramedullary lengthening nails exhibit a high complication rate of 60% and an average rate of about 30%, manifesting issues such as nail breakage, blood loss or infection at the osteotomy site, fracture upon implantation and pain. Soft tissue stress, abnormal bone growth, and other complications may also be associated with the continuous distraction of the femoral shaft beyond 8 cm. Furthermore, intramedullary nails are not a viable solution for patients requiring total joint arthroplasty or those who suffer from post-total-hip-arthroplasty Limb Length Discrepancy. There is no total joint implant currently available that is capable of non-invasively adjusting the length of the surgical limb without revision surgery. There is a need for a non-invasive solution to anticipate and correct Limb Length Discrepancy in patients who have had or would benefit from total joint arthroplasty.

SUMMARY OF THE INVENTION

The invention provides a total joint prosthesis configured for adjusting the length of a limb. In one embodiment, the total joint prosthesis includes a stem, a housing, and a neck. The housing is configured for insertion into an intramedullary space of a resected long bone. The stem includes the housing within. The housing includes a rotatable magnetic rod. The rod is axially coupled to an input gear. The housing further includes a first gear set comprising a first plurality of parallel spur gears axially coupled to a first non-magnetic rod. A first spur gear receives the input gear. The housing further includes a second gear set comprising a second plurality of parallel spur gears axially coupled to a second non-magnetic rod. The gears of the first and second gear sets are parallel and intermesh. A last spur gear is received by an output gear. The housing further includes a lengthening screw having a first portion disposed within the housing and a second portion extending out of the housing. The first portion is axially coupled to the output gear. The neck has a proximal part and a distal part, wherein the distal part comprises a threaded internal cavity along a length thereof configured for receiving the second portion of the lengthening screw. The proximal part couples to an implant head configured for insertion into a joint socket.

In another embodiment, the adjustable device includes an external adjustment device with at least one rotatable magnet. In another embodiment, the external magnetic device can include two large magnets and one small magnet, wherein the small magnet is perpendicular to the two large magnets.

In another embodiment, a first section of the distal part of the neck can be housed within a telescopic shaft. In a related embodiment, the neck further includes a bearing to secure the lengthening screw. The distal part of the neck can be a hexagonal cylinder further including grooves. The telescopic shaft can be a hexagonal cylinder further including inward protrusions, such that the protrusions of the distraction shaft fit into the grooves of the distal neck. Rotation of the magnetic rod in a first axial direction through a plurality of rotations causes the neck to move toward the housing, and rotation of the magnetic rod in a second direction through a plurality of rotations causes the neck to move away from the housing.

In another embodiment, the gear ratio of the first and second gear sets can range from 1:500 to 1:2000. The input gear can be a worm gear. The stem further includes, in one example, a porous coating. In one embodiment, the long bone can be a femur and the joint socket can be an acetabulum.

In yet another embodiment, a length-modulating medical implant device includes a stem, a gearbox housing, and a neck. The stem further includes a proximal stem and a distal stem. The proximal stem includes a rectangular box portion and a lateralized edge. The rectangular box portion of the stem is wider laterally than the distal portion of the stem, causing the box to protrude or extend slightly further out from the lateral side of the femur. This feature allows a lateral surface of the box to act as a lateralized ledge, which can be used as an impaction point during implantation. The rectangular portion is hollow. The distal stem is operatively connected to the proximal stem. The distal stem tapers gradually in a triangular manner. A vertical axis of the distal stem parallels a patient's femur. The housing is situated within the rectangular portion of the proximal stem. The housing includes a plurality of compartments configured to house a length-modulating mechanism. The neck is operatively connected to the proximal stem. The neck further includes a distal portion and a proximal portion. The distal portion is a hexagonal cylinder operatively connected to a lengthening screw. The proximal portion is a sphere. The proximal portion further includes a hexagonal hole adapted to accept the neck. Alternatively, the rectangular portion of the proximal stem can include a 30 mm hexagonal outpouching or telescopic shaft. The neck can be seated within the hexagonal outpouching upon shortening of the length-modulating medical implant device.

Furthermore, the lengthening mechanism can include a magnetic input rod, a magnetic output rod, a series of two gears, and a step motor. An input force results from rotating the magnetic input rod. An output force results in length modulation. The magnetic output rod is circumferentially connected to a spur gear. The series of gears can be parallel to one another. The series of gears can be placed in between the magnetic input rod and the magnetic output rod.

The invention provides a method of treating limb-length discrepancy with a length adjustable total joint prosthesis. In one embodiment, the prosthesis includes a housing with a rotatable magnetic rod mechanically coupled to a lengthening screw. The lengthening screw interfaces with an implant neck such that rotation of the magnetic rod causes the lengthening screw to either compress the neck toward the housing or extend the neck away from the housing. The method includes making an incision in a patient's skin in proximity to a ball-and-socket joint of a first limb. The joint includes a proximal portion of a long bone and a joint socket. The method further includes resecting the proximal portion of the long bone and inserting the prosthesis into the joint. Inserting includes impacting a first part of the prosthesis into the long bone and a second part into the joint socket. The method further includes closing the incision. The method further includes determining a length discrepancy in the first limb. Determining a length discrepancy includes determining that the first limb is longer than a second limb, that the first limb is shorter than the second limb, or that the first limb and second limb are of equal lengths. This can be done using a full-length x-ray combined with biomechanical measurement software, or it can be done using 1 mm step blocks that the patient will place under the shorter limb until they feel as though their limbs are equal. The method further includes placing an external device comprising at least one rotatable magnet over the skin in proximity to the joint. The method further includes operating the external magnetic device so that a magnetic field of the at least one rotatable magnet causes the magnetic rod of the prosthesis to rotate, causing the lengthening screw to move the neck either toward or away from the housing, such that a length of the limb is adjusted.

In some embodiments, operating the external magnetic device further includes causing the lengthening screw to rotate in 1 mm increments. The lengthening screw can be caused to rotate in a first axial direction, causing the neck to move toward the housing such that the overall length of the limb is decreased. The lengthening screw can be rotated in a second axial direction, causing the neck to move away from the housing such that the overall length of the limb is increased.

In other embodiments, inserting the prosthesis into the joint further includes inserting a liner into an intramedullary space of the long bone and impacting a stem into said liner, securing the lengthening screw into the neck and impacting an implant head into the joint socket.

One aspect of the present disclosure is directed to a length-adjustable total joint prosthesis, comprising: (a) a housing disposed within a stem, wherein the stem is configured for insertion into an intramedullary space of a long bone, wherein the housing comprises: (i) a permanent magnetic rod configured for circumferential rotation, wherein the rod is rotationally coupled to an input gear, (ii) a first gear set comprising a first plurality of parallel spur gears, wherein the first gear set is operatively coupled to the input gear, (iii) a second gear set comprising a second plurality of parallel spur gears, wherein the first and the second gear sets intermesh in parallel, and (iv) a lengthening screw having a first portion disposed within the housing and rotationally coupled to the output gear and a second portion extending out of the housing; and (b) a neck comprising a threaded internal cavity along a length thereof configured for receiving the second portion of the lengthening screw, wherein a proximal part of the neck is configured for coupling to an implant head, and the implant head is configured for insertion into a joint socket. In one embodiment, said neck comprises a neck operatively connected to the proximal stem, further comprising a distal portion and a proximal portion, wherein the distal portion is a hexagonal cylinder connected to a lengthening screw, wherein the proximal portion is a sphere, further comprising a hexagonal hole of a hexagonal cylinder cavity wherein a lengthening screw is attached between the neck's proximal and distal parts and implant head that has a hexagonal shaped hole therein allowing for coupling between the neck and the implant head, wherein the implant is inserted into the joint socket.

In one embodiment, the device further comprises an external adjustment device comprising at least two rotatable permanent magnets. In another embodiment, the operation of the external adjustment device over a patient's skin generating a magnetic force that causes rotation of the magnetic rod. In one embodiment, the device further comprises a telescopic shaft, wherein the shaft houses the second portion of the lengthening screw and a distal part of the neck. In another embodiment, the lengthening screw is coupled for rotation within the neck by a bearing. In a related embodiment, the neck is a hexagonal cylinder further comprising grooves, and wherein the telescopic shaft is a hexagonal cylinder further comprising an inward protrusions, such that the protrusions of the shaft fit into the grooves of the neck.

In one embodiment, rotation of the magnetic rod in a first axial direction through a plurality of rotations causes the implant neck to move toward the housing to effect a decrease in a length of the prosthesis, and wherein rotation of the magnetic rod in a second direction through a plurality of rotations causes the implant neck to move away from the housing to effect an increase in a length of the prosthesis. In another embodiment, a gear ratio of the first and the second gear sets ranges from about 1:500 to 1:2000. In one embodiment, a lateral surface of the housing comprises a lateralized ledge. In another embodiment, the stem further comprises a porous coating. In one embodiment, the long bone is a femur and the joint socket is an acetabulum.

Another aspect of the present disclosure is directed to a length-modulating medical implant device comprising: (a) a stem further comprising a proximal stem and a distal stem, wherein the proximal stem includes a rectangular portion and a lateralized edge, wherein the rectangular portion is hollow; wherein the distal stem is operatively connected to the proximal stem, wherein the distal stem tapers gradually in a triangular manner, wherein a vertical axis of the distal stem parallels a patient's femur; (b) a gearbox housing situated within the rectangular portion of the proximal stem wherein the housing includes a plurality of compartments configured to house a length modulating system; and (c) a neck is operatively connected to the proximal stem, further comprising a distal portion and a proximal portion, wherein the distal portion is a hexagonal cylinder operatively connected to a lengthening screw, wherein the proximal portion is a sphere, further comprising a hexagonal hole adapted to accept the neck.

In one embodiment, the neck is connected to a proximal stem with a base and containing a conical shaped distal portion and a rectangular based proximal portion that attaches to a mechanical gearbox, wherein the distal portion contains a hexagonal cylinder holding screw adjustable in length; wherein the proximal portion is a sphere containing a hexagonal-shaped hole to allow for surgical connection between the screw and the joint socket. In one embodiment, the rectangular portion of the proximal stem includes a 30 mm hexagonal outpouching, wherein the neck is seated within the hexagonal outpouching upon shortening of the length modulating medical implant device. In another embodiment, the lengthening mechanism further comprises: a magnetic input rod, wherein rotation of the magnetic input rod in either a first or a second direction creates an input force; a magnetic output rod, wherein an output force results in length modulation, wherein the magnetic output rod is circumferentially connected to a spur gear; a series of two gears, wherein the gears are parallel to one another, wherein the series of gears are in between the magnetic input rod and the magnetic output rod; and a step motor.

One aspect of the present disclosure is directed to a method of treating limb-length discrepancy with a length-adjustable total joint prosthesis comprising: (a) making an incision in a patient's skin in proximity to a ball-and-socket joint of a first limb; (b) performing a total joint arthroplasty, wherein performing the total joint arthroplasty comprises impacting a first part of the prosthesis into an intramedullary space of a resected long bone and a second part of the prosthesis into a joint socket, wherein the prosthesis comprises a gearbox housing comprising a rotatable magnet mechanically coupled to a lengthening screw, the lengthening screw configured for moving a neck about a vertical axis either toward or away from the housing; (c) closing the incision; (d) determining a length discrepancy in the first limb, wherein determining comprises determining that the first limb is longer than a second limb, that the first limb is shorter than the second limb, or that the first limb and the second limb are of equal lengths; and (e) operating an external magnetic device comprising a magnetic field of at least one rotatable magnet, wherein the magnetic field rotates the magnetic rod of the prosthesis, causing rotation of the lengthening screw such that the neck is moved either toward or away from the housing, thus increasing or decreasing the resistance, such that an overall length of the first limb is adjusted.

In one embodiment, operating the external magnetic device further comprises causing the lengthening screw to rotate in 1 mm increments. In another embodiment, inserting the prosthesis further comprises measuring a natural length of a long bone neck; and partially inserting a distal part of the implant neck into a telescopic shaft, such that a combined length of the telescopic shaft and the distal part of the implant neck is equal to said natural length. In one embodiment, the lengthening screw is caused to rotate in a first axial direction, causing the neck to move toward the housing such that the overall length of the limb is decreased. In another embodiment, the lengthening screw is caused to rotate in a second axial direction, causing the neck to move away from the housing such that the overall length of the limb is increased. In another embodiment, inserting the prosthesis into the joint further comprises inserting a liner into an intramedullary space of the long bone; impacting a stem into said liner; securing the lengthening screw into the neck; and impacting an implant head into the joint socket.

DETAILED DESCRIPTION

I. Hip Prosthesis

Figure 1:
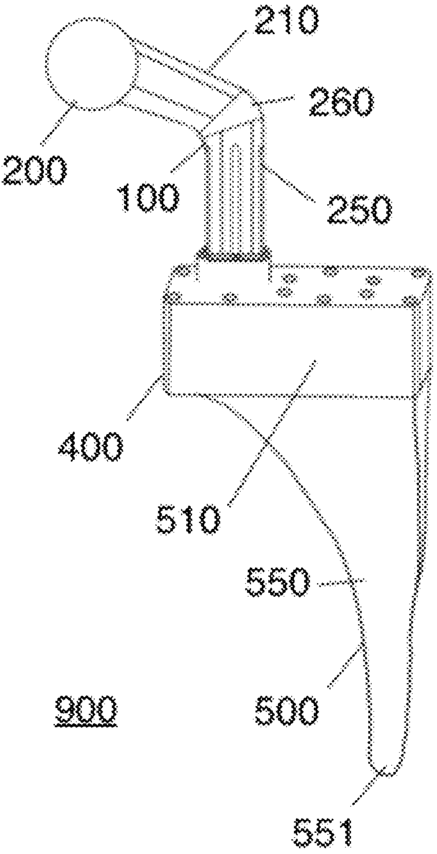
FIG. 1 is a perspective view of a length modulating medical implant device, showing a neck, housing, and stem.
Figure 5:
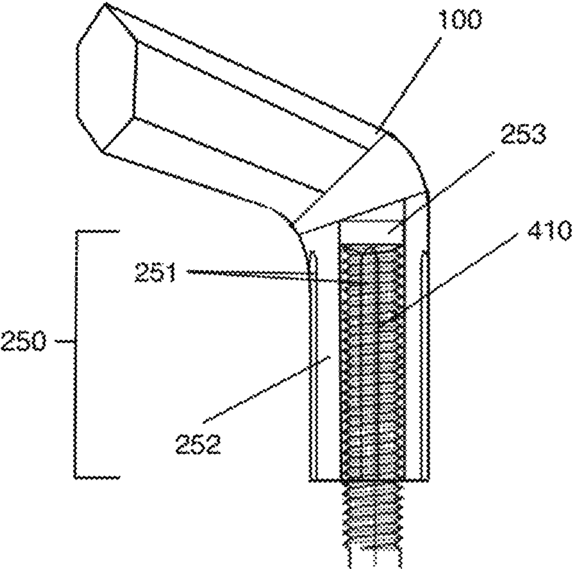
FIG. 5 is a cross section view of the neck, showing a portion of a lengthening screw disposed within, via threading.
Figure 9:
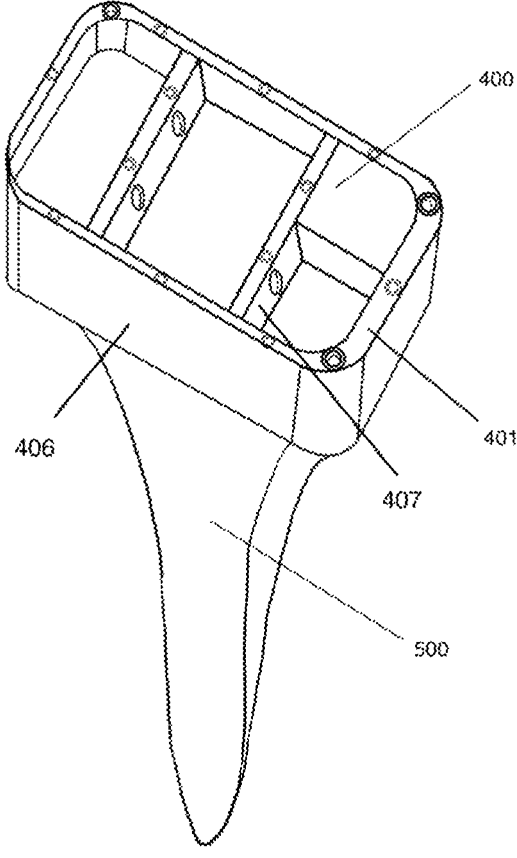
FIG. 9 is a perspective view of the housing and stem, showing compartments within the housing when it is hollow.
Figure 10:
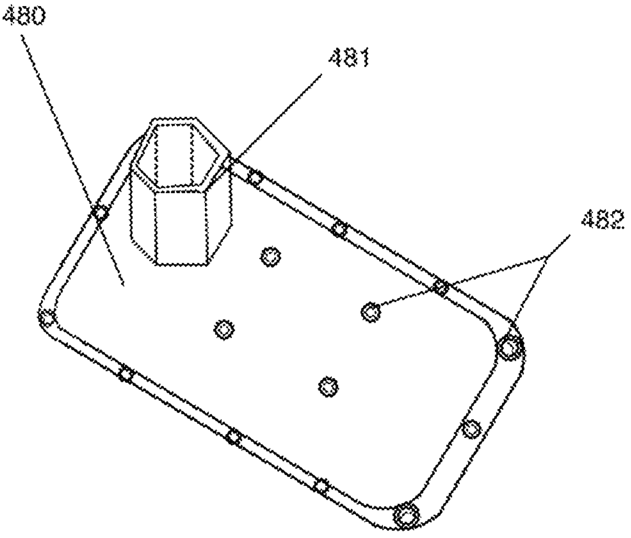
FIG. 10 is an elevated top view of the housing, showing the housing covered and the cover secured via screws, and showing the base of the telescopic shaft.
Figure 11:
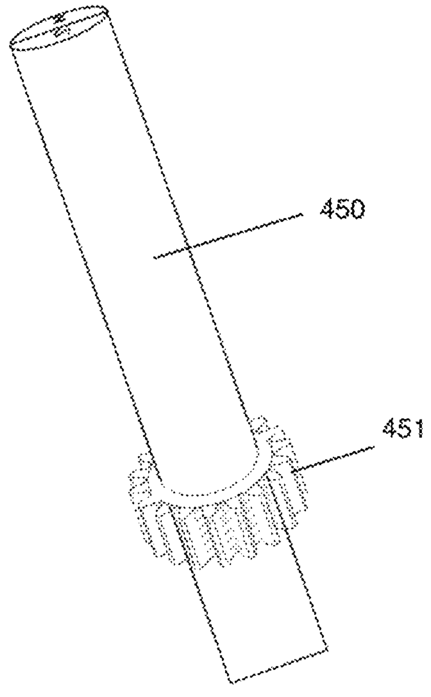
FIG. 11 is a perspective view of the magnetic rod, showing a gear secured to it.

FIG. 1 illustrates a perspective side (anterior) view of a length-modulating total joint prosthesis 900 configured for replacement of the acetabulofemoral joint. The hip prosthesis 900 illustrated in FIG. 1 includes a stem 500, a gearbox housing 400, a neck 200, and an implant head 200. The stem includes a distal portion 550 and a proximal portion 510. The distal stem 550 is conical in shape and tapers into a tip 551 for ease of insertion and to enable press-fit implantation. The proximal stem 510 is rectangular and includes a hollow rectangular housing that contains a lengthening mechanism 400 (FIG. 9). An implant neck 100 includes a threaded internal cavity within its distal part 250 configured for mechanical coupling to the lengthening mechanism 400 (FIG. 5). The neck 100 exhibits a 126-degree bend 260 between its distal part 250 and proximal part 210. The proximal part of the neck 210 couples to an implant head 200, which is impacted into an acetabulum during insertion of the prosthesis 900.

Figure 2:
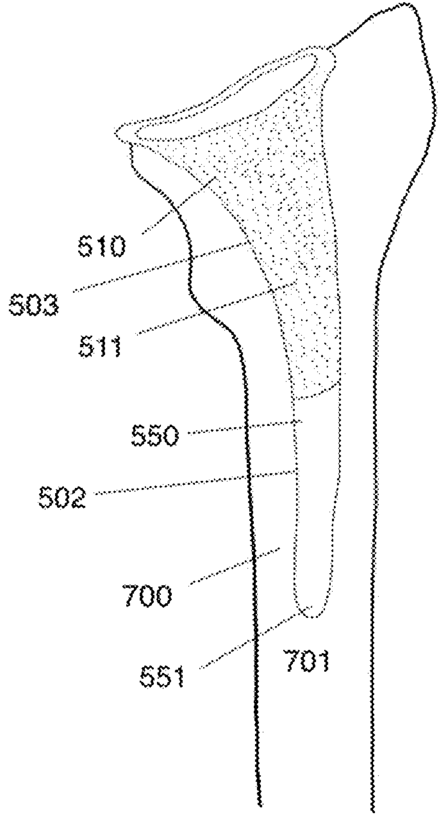
FIG. 2. is a cross section view of the stem, showing the stem implanted into the limb of a patient.

In FIG. 2, a femoral head and neck are resected and an intramedullary space 701 of the femur is reamed, or drilled to evacuate an intramedullary space to accommodate the prosthesis to be inserted. In one embodiment, a liner 502 is inserted into the intramedullary space prior to implanting the stem 500 (FIG. 1). The liner 502 is a titanium socket that is coated with a porous grit-blasted coating 511 and $Ca(PO_4)$ bio-gel for optimal ingrowth of cortical bone. The stem 500 (FIG. 1) is implanted into the liner 502 and the liner 502 houses the stem 500 tightly. The vertical axis of the liner 502 parallels that of the femur 700. It is conical in shape and tapers conically into a tip 551 at its distal end 550. In an embodiment where a liner 502 is included, the liner 502 can be 2 mm wider than the width of the stem 500 (FIG. 1) measuring medially to laterally to enable a secure fit. The proximal portion 503 of the liner 502 is fluted and caps the medial and lateral cortices of the femur 700 like a collar. In another embodiment, a liner 502 is not used and the stem 500 (FIG. 1) includes a grit-blasted porous coating, wherein the porous coating includes a $Ca(PO_4)$ bio-gel.

Figure 3:
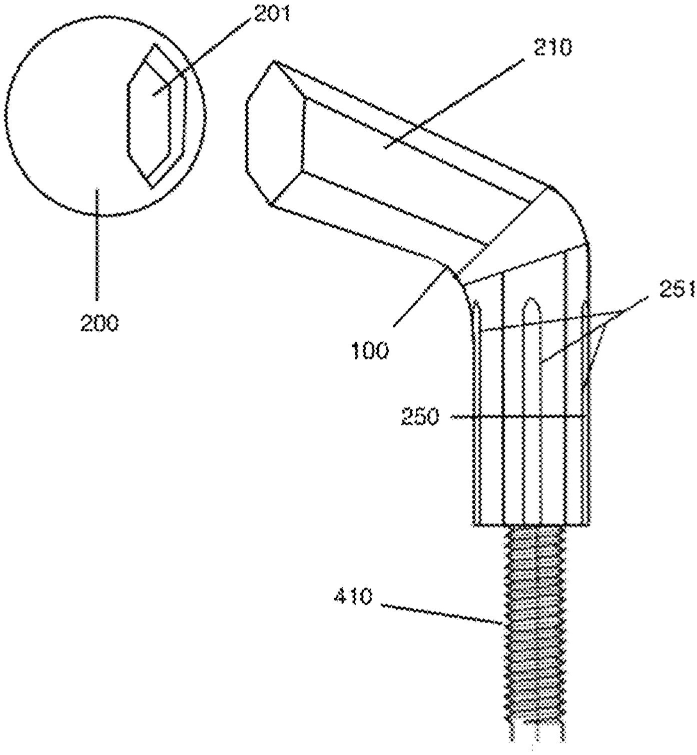
FIG. 3 is a perspective view of the neck and a head, showing the hexagonal shape of the neck and corresponding hexagonal hole of the head for connection of the two.
Figure 4:
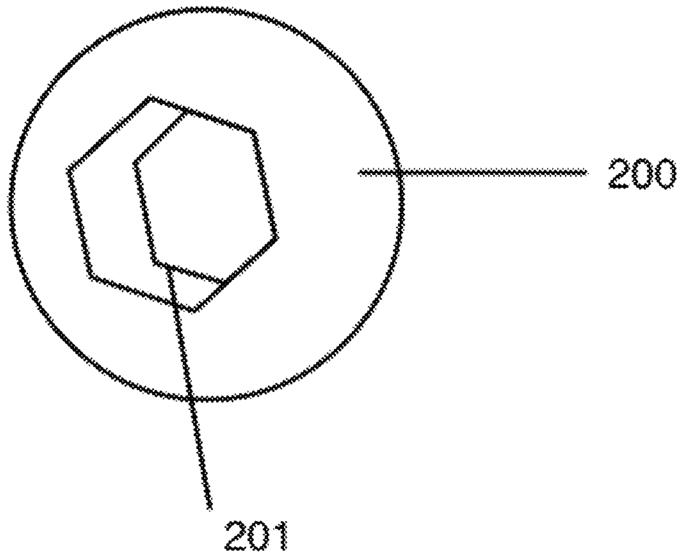
FIG. 4 is an elevated side view of the head, showing the hexagonal hole.

FIGS. 3-4 illustrate a proximal portion of a length-modulating total joint prosthesis 400 (FIG. 1). As shown in FIG. 3, the neck 100 is assembled in a single molding. It can be attached to the lengthening screw 410 during manufacturing. It may also be attached intraoperatively. The implant neck 100 includes a proximal part 210 and a distal part 250. The distal part 250 can be 35 mm in length and the proximal part 210 can be 30 mm in length. A 126-degree bend 260 between the proximal and distal parts allows the implant neck 100 to mimic the anatomy of the natural femoral neck. The proximal part 210 of the neck 100 couples to an implant head 200. In one embodiment as shown in FIG. 3, the implant neck 100 is a hexagonal cylinder and the implant head 200 includes a hexagonal hole 201 for coupling to the neck 100. During total hip arthroplasty, the head 200 is impacted into the joint socket or acetabulum using conventional methods.

FIG. 5 shows the structural relationship between the distal portion of neck 250 and a lengthening screw 410. The distal portion of the neck 250 includes a threaded internal cavity that receives the lengthening screw 410. In one embodiment, there is a lip at the proximal end of the screw that inserts into an indentation in the internal wall of the neck 100. In another, there is a secure bearing within the neck that allows rotation but secures the screw to avoid displacement. The internal cavity can be 10 mm wide and 25 mm long to accommodate the lengthening screw 410, with thread pitching proportional to that of the lengthening screw 410.

The thread pitch of the lengthening screw 410, and the corresponding threading of the neck, may be in a range from between 0.5 mm to 1 mm. Fine pitching in the rod can prevent back-driving of the neck once ideal length-modulation is achieved. The lengthening screw 410 can compress or extend the neck 100, moving it toward or away from the gearbox housing. The screw 410 is secured to the neck 100 in a way that allows rotation of the screw 410 within the neck 100, but also pushes the neck 100 in retrograde motion, and pulls the neck 100 in anterograde motion. The neck 100 is configured for vertical movement about an axis parallel to the vertical axis of the femur 700 (FIG. 2). The neck 100 can be implanted in a partially extended state, so that it may compress 20-30 mm if necessary.

Figure 6:
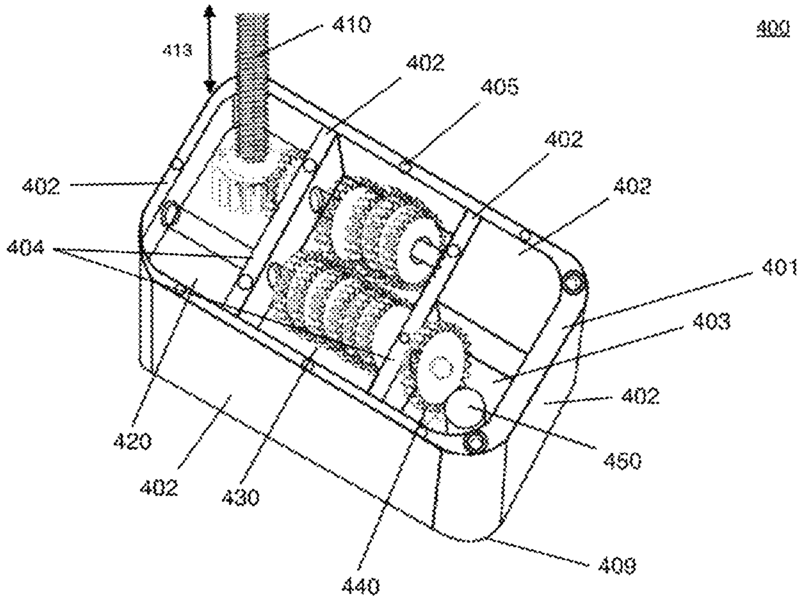
FIG. 6 is an elevated top view of the housing showing the plurality gear sets intermeshed.

FIGS. 5-6 illustrate a telescopic shaft 252 which houses the distal part of the neck 250 and the portion of the lengthening screw 410 extending out of the gearbox housing 400. The telescopic shaft 252 can comprise a series of interconnected sections that are capable of telescopic extension away from the housing 400, thereby increasing the length of the implant and limb. The telescopic shaft 252 can also reverse-telescope from an extended state toward the housing 400, thereby decreasing the length of the implant and the limb. Both the telescopic shaft 252 and the neck 250 can have the shape of a hexagonal cylinder. The hexagonal design was adopted over a traditional cylindrical design because the Applicant discovered through experimentation that this will reduce shear forces along the neck 250 as it extends and be yet another feature of the proposed prosthesis that improves upon existing available options.

The distal part of the neck further comprises grooves 251 which couple to inward protrusions disposed within the telescopic shaft 252 to increase the surface area of interaction between the two components and reduce shear forces. In one embodiment, there can be six grooves 251 that run vertically along the distal part 250 and are 1 mm wide, 1 mm deep, and 151 mm long. The protrusions that couple the grooves 251 can have equal dimensions. In one embodiment, there are six 1 mm wide, 1 mm deep, 151 mm long inward protrusions that run vertically along the inner walls of the telescopic shaft 252. These fit inside of 1 mm wide, 1 mm deep, 151 mm long grooves along the outer walls of the neck, conceived this way so as to increase the surface area of interaction between the two components and reduce shear force.

Before assembling the device, the natural femoral neck length of the patient can be measured. The implant neck 250 can be inserted into the telescopic shaft 252 to a customizable depth. The neck 250 can be inserted completely or only partially into the telescopic shaft 252. When the neck 250 is partially inserted, there is a portion of the neck 250 housed within the telescopic shaft 252, and a portion of the neck 250 extending out of the shaft. This enables an operator to customize the total length of the shaft 252 and the portion of the neck 250 extending out of it, such that the total length matches the natural length previously measured.

Figure 7:
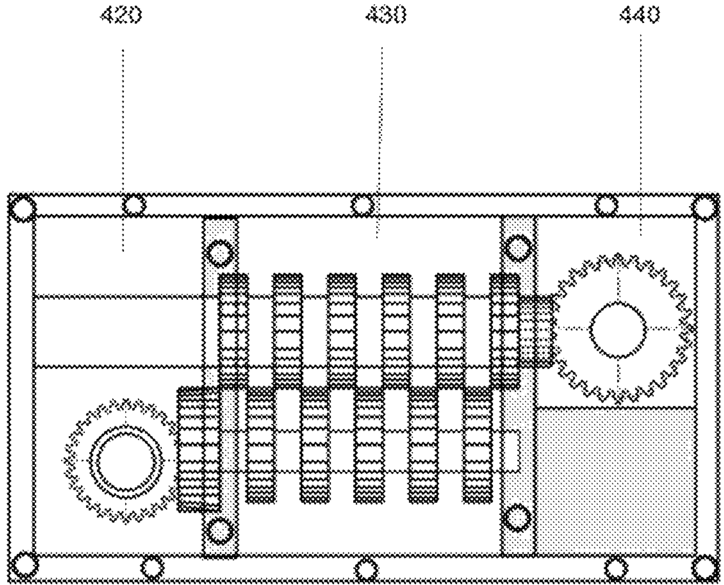
FIG. 7 is an elevated top view of the intertwined gear sets.

As shown in FIGS. 6-10 the gearbox housing 400, which is within the rectangular hollow portion of the stem 100, contains the lengthening mechanism. The housing can have adjacent compartments to house the components of the lengthening mechanism. Specifically, the gearbox housing includes two interlocking components 411, 476 and 451, 461. As depicted in FIG. 9, which shows the compartments of the gearbox housing when they are empty, the bottom component 409 is continuous with the stem 500 and can be manufactured of titanium alloy, similar to the stem. As shown in FIG. 6, The bottom component 409 includes the transverse floor 403 and six vertical walls 402 of the gearbox housing. As shown in FIGS. 6-7, The internal walls 404 subdivide the gearbox into three chambers 420, 430, 440. The walls can be 2-4 mm thick on the vertical sides. A plurality of screw holes 405 can be found throughout the gearbox housing that allows the bottom floor and lateral walls to be affixed to the top plate 480, which encloses the lengthening mechanism within the gearbox housing.

Figure 12:
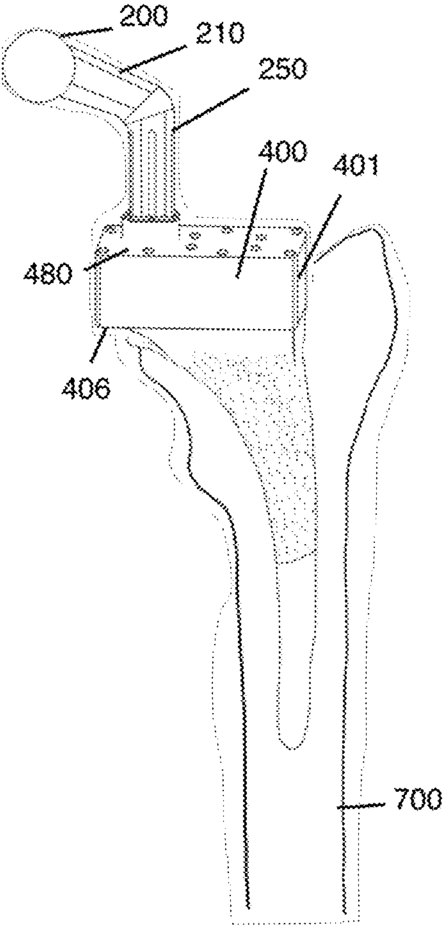
FIG. 12 is a front view of the external magnetic device, showing a screen for controlling the lengthening mechanism.

As shown in FIG. 12, the gearbox housing 400 does not enter the medulla of the bone, rather it is configured to sit between the vertical axes of the lesser trochanter and greater trochanter, filling the space below where the former anatomical femoral neck lay. This is the same space that a traditional total hip implant occupies, but the medial edge may protrude medially or laterally from the femur. The size of the gearbox housing 400 does not impinge on any medial anatomical structures. The gearbox volume is consistent in size throughout all sizes of the implant offered. The gearbox housing further includes a lateral edge 401 which may thicken slightly in implants with greater offsets, however, the volume of the gearbox housing remains the same. In certain embodiments, the top plate 480 can be securely screwed onto the bottom plate 406 using 12 screws that secure the corners, and 8 screws to secure top grooves to gearbox walls. In one embodiment, a silicone or polyethylene cap that can be attached to the bottom of the top plate 480 along the edges and grooves to provide a secure, waterproof seal once the top plate is screwed in. The top plate can be made of 2-4 mm thick titanium alloy.

As shown in FIG. 9 the base of the gearbox housing 400 features small shafts to house bearings for the magnetic rod 450, accompanied by a similar shaft on the top plate 480 to house the top of the magnetic rod 450. The medial wall has a shaft housing and a bearing for transverse rod A 460. The lateral plate 407 has a similar shaft to house the bearing for securement of transverse rod A 460. These shafts can be 5 mm.

Figure 8:
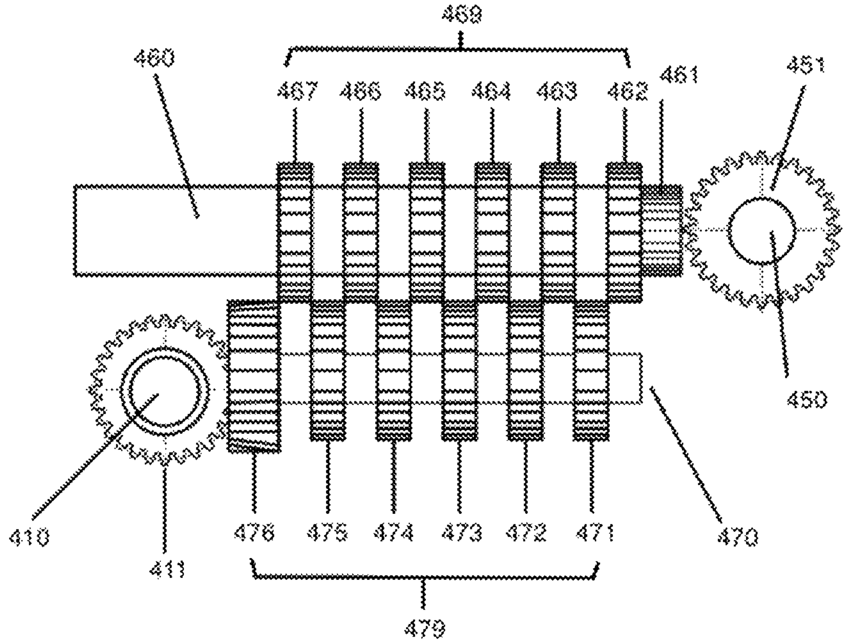
FIG. 8 is a perspective view of the housing, showing a plurality of gear sets, the lengthening screw, and a magnetic rod within.

As shown in FIG. 6-8 the lengthening mechanism 400 further includes a magnetic input rod 450, a magnetic output rod 410, and a series of two sets of gears 469, 479. In certain embodiments the lengthening mechanism may include a step motor. An input force results from rotating the magnetic input rod 450. An output force results in length modulation 413. The magnetic output rod 410 is circumferentially connected to a spur gear. The two sets of gears 469, 479 can be parallel to one another. The series of gears 469, 479 can be placed in between the magnetic input rod 450 and the magnetic output rod 410. The input force results from the rotation of a 1.5" magnetic rod attached to spur gear that encircles it along its horizontal axis.

The spur gear 473 interacts with a vertical gear located medially. The vertical gear 461 has a hole in the middle so that it may fix to a transverse rod 470 that runs the length of the gearbox housing 400 from the magnetic rod 450 to the medial wall. The transverse rod 460 holds a plurality of gears that make up a first gear set 469. This can include 6 parallel, interlocking gears that encircle the rod. These gears do not rotate about the transverse rod 460. Rather, they are fixed to the rod, which turns along with the gears. These gears (462, 463, 464, 465, 466, 467) are oriented in the sagittal plane. The transverse rod 460 can be secured on the medial end of the gearbox 400 with a bearing. The gears of the first and second spur gear sets intermesh in parallel. The gears of each gear set are parallel to each other, and each set is parallel to the other. The teeth of the gears of the first gear set intermesh with the teeth of the gears of the second gear set. The intermeshing gear sets can be said to form a gear train, a drive train, or a gear transmission. The intermeshing gear sets thus function to transmit a force received from the rotating magnetic rod into the lengthening screw. The gear ratio of these gear sets may be adjusted to affect the speed of rotation and force-transmitting capacity.

FIG. 8 illustrates a cross-section view inside the lengthening mechanism 400 of FIG. 6. Three gears (gears 471, 472, 473) are posteriorly displaced and are secured by a second transverse rod 470. These articulate with the gears 462, 463, 464, 465, 466, 467. Gear 471 is located between gears 464 and 465 and overlaps by about 3 mm. Gear 472 is located between gears 465 and 472, similarly overlapping with them by 3 mm. Gear 473 is located between gears 466 and 467, and overlaps these gears by 3 mm. The second transverse rod 470 is fixed by a bearing to the lateral wall. It connects with the lengthening rod 410 via two spur gears 473, 475. One spur gear (gear 473) in fixed around the second transverse rod 470. The other spur gear (gear 475), which is at a 90-degree angle to spur gear 473, is fixed to the lengthening rod 410. The inner wall of spur gear 475 can be threaded into the lengthening rod 410.

Referring to FIG. 12, the magnetic rod rotation is controlled by an external magnetic device 600 (FIG. 13), which features a magnet 613 that parallels the magnetic rod 410. The magnetic field 621, 622 produced by the external device turns the magnetic rod 450 about its vertical axis within the gearbox housing 400. The magnetic rod is rotationally coupled to an input gear, which can be a worm gear, such that the gear rotates in the same axial direction as the rod when the rod rotates. The gear that is fixed to the rotating magnet interacts with gear 461 at a 90-degree angle and causes sagittal rotation. Rotation of gear 461 causes rotation of the transverse rod 470, causing the 9 gears in chamber B 430 to turn. Finally, the turning of gear 473 interacting at 90 degrees with gear 475, rotates the lengthening screw 410 anterograde or retrograde, which is dependent on the magnetic field 621, 622 produced by the external device.

Figure 16:
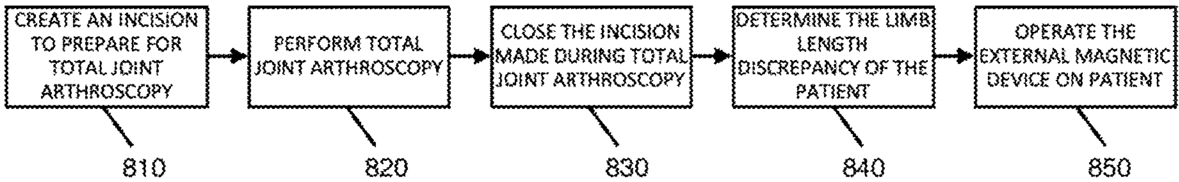
FIG. 16 describes the incision step of the intraoperative protocol.

FIG. 16 illustrates the method of using the length-modulating joint prosthesis is further explained below. For surgical implantation of the length-modulating joint prosthesis, the posterior approach can be used because it allows for optimal visibility and space for implantation. In this approach, the patient is placed in the lateral decubitus position. The surgical leg is non-restrictively draped to allow limb movement throughout the procedure.

FIG. 16 describes the incision step 810. Specifically, an incision is made 5 centimeters distal to the greater trochanter, centered on the femoral diaphysis. The incision is continued proximally up to the greater trochanter. Once the greater trochanter is reached, the incision is curved toward the posterior superior iliac spine for approximately 6 centimeters. At that point, it curves toward the posterior superior iliac spine for 6 centimeters. The tensor fascia latae superficial to the gluteus maximus is then incised deep to the short external rotators. A retractor is positioned to retract the gluteus maximus. The sciatic nerve is observed and avoided. Next, the short external rotators and piriformis are then given a tenotomy at the greater trochanteric insertion, revealing the posterior capsule. A suture is used to mark these tendons for identification after implantation. The posterior capsule is incised to reveal the femoral neck and head. The joint capsule may also be incised with the short external rotators in a single layer during tenotomy.

Figure 16A:
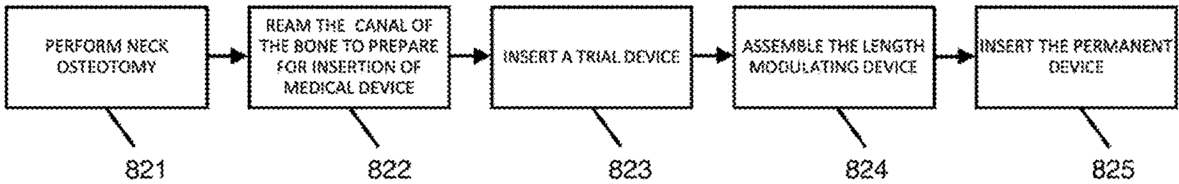
FIG. 16A describes the performing total joint arthroscopy step of the intraoperative protocol FIG. 16B describes the limb length discrepancy step of the post-operative protocol
Figure 16B:
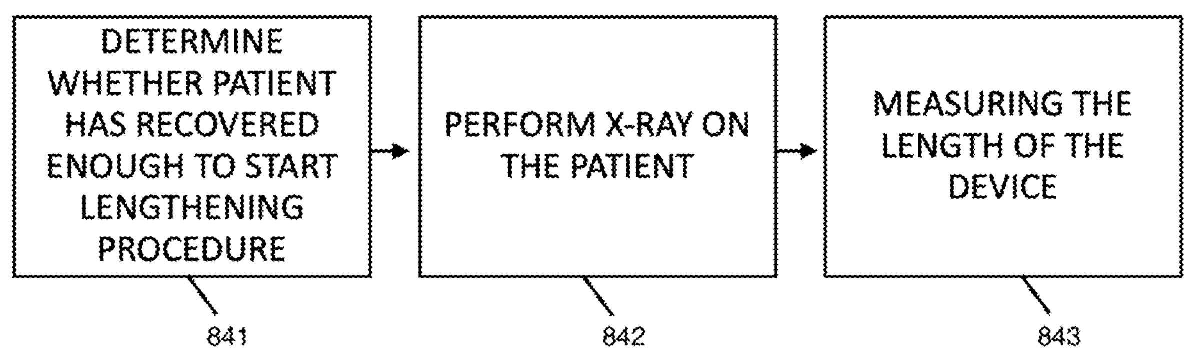

FIG. 16A further describes the performing total joint arthroscopy step 820 as shown in FIG. 16. In step 821, the femoral head is then dislocated by internally rotating the hip. A femoral neck osteotomy is then performed using a reciprocating saw. Retractors are placed anteriorly and posteriorly to protect soft tissues from the saw blade. The severed femoral head is removed, and the acetabulum and proximal femur are observed freely. Retractors are placed around the acetabulum for visibility. The acetabulum is then prepared, and the cup and temporary liner are press-fit. It is postulated that this would provide for the most success post-operative compared to screwing or cementing any part of the implant. The liner functions to improve securement of the implant into the intramedullary space. In another embodiment, a liner may not be used, and the stem may be coated in a porous substance to promote ingrowth of cortical bone.

Next, in step 822, the leg is internally rotated, flexed and slightly adducted to expose the proximal femur. Femoral preparation is completed, which includes successive reaming of the canal to a predetermined size. A technique that uses calcar reaming to ensure load transfer that avoids excessive load on the base of the implant neck is performed. This method will ensure medial cortical bone growth that will protect the modular components of the gearbox housing 400 and neck 100 (FIG. 1). A liner is then compacted into the intramedullary space. Next in step 823, a trial implant for size evaluation is compacted into the liner. A trial head is compacted onto the trial implant, and the joint is relocated. Trial models are used to evaluate sizing for stability and length, and are manipulated to test stability in each field of motion. The trial implants are removed if manipulation is satisfactory. If not, new trial implants of different sizes are tested. Next in step 824, The assembly of the permanent implant succeeds this step. Before implanting the permanent implant 900 as shown in FIG. 1, the stem 500, gearbox housing 400 and neck 100 of the device must be assembled intraoperatively. The stem of the implant is molded in a single piece.

The base of the gearbox housing 400 is continuous with the stem 500. The gears sets 469 (FIG. 8), 479 (FIG. 8) and lengthening mechanism components are assembled and placed into the gearbox housing 400 (FIG. 1). As shown in FIG. 6, The magnetic rod 450, transverse rod 460, and lengthening screw 410 are secured with bearings to the base and walls of the gearbox housing 400. As shown in FIG. 8, A worm gear 451 is welded to the magnetic rod 450 that interacts with a vertical gear on the transverse rod 460 that runs through the length of the housing 500. The transverse rod 500 is supported by both the gear mechanisms it connects to (on the magnetic rod 450 and lengthening screw 410), and two bearings that run in the sagittal plane within the inner walls or grooves of the gearbox housing 400. The gears 463, 464, 465, 466 in the middle compartment 430 are placed along the transverse rod 460 during assembly. The lengthening screw 410, similarly, is placed in the gearbox housing 400 during assembly, secured with bearings, and inserted into the neck 100 of the implant by press fit once the top plate is secured to the stem 500 with screws.

Lastly in step 825, a permanent implant 900 (FIG. 1) is impacted into the liner 502 (FIG. 2). The permanent implant neck 100 (FIG. 1) will be extended at a minimum of 15 mm to anticipate post-operative Limb Length Discrepancy. However, this will not cause Limb Length Discrepancy, as the extended model will match the patient's anatomy. The permanent head 200 (FIG. 3) is impacted onto the neck. The trial acetabular liner is removed, and a permanent polyethylene liner 502 (FIG. 3) is impacted. Finally, the joint is relocated and manipulated for stability.

FIG. 16 describes the performing closing step 830. Specifically, to close, the short external rotators and posterior capsule are repaired through transosseous bone tunnels in the proximal femur or a direct repair to soft tissues, and the fascia and skin are closed using sutures. Alternatively, the superficial skin incision can be closed using staples or Dermabond.

FIG. 16 describes the determining limb length discrepancy step 840. Specifically, the lengthening procedure which starts by determining the limb length discrepancy could proceed after closure and while the patient is awake. This procedure could be started, for example, a day after the surgery when the patient has recovered from anesthesia. Alternatively, the lengthening procedure could be started a week after the surgery when the patient has fully recovered from the surgical procedure. Alternatively, it could also be done weeks after the surgery, after significant tissue healing has occurred. To determine the appropriate size of implant, a pre-operative AP Xray of the pelvis is taken and uploaded into a templating software, depending on the preference of the physician. In this embodiment, measurements are taken of the femoral offset, neck length, medulla width, and head diameter. These measurements are compared with standardized sizes of the implant, and an ideal implant size is chosen to closely match patient anatomy.

The gear ratio per patient varies per person which depending on the lengthening time determined by the care provider and the comfort of the patient. Clinically, a certain amount of error is feasibly tolerated (approximately 5 mm), therefore the gear ratio is customizable, dependent on case-by-case tolerability. In one embodiment, there can be 15 gears in total and a gear ratio of 1:1159. In other embodiments, the gears per parallel set 460 (FIG. 8), 479 (FIG. 8) may range from 6-12 gears. As such, in other embodiments, the gear ratio ranges from 1:500-1:2000. In addition to the number of gears, gear size also affects gear ratio such that increasing the gear size decreases the velocity of distension but increases the torque output. In one embodiment, the prototype allows for approximately 30 minutes per 1 mm distension.

Figure 13:
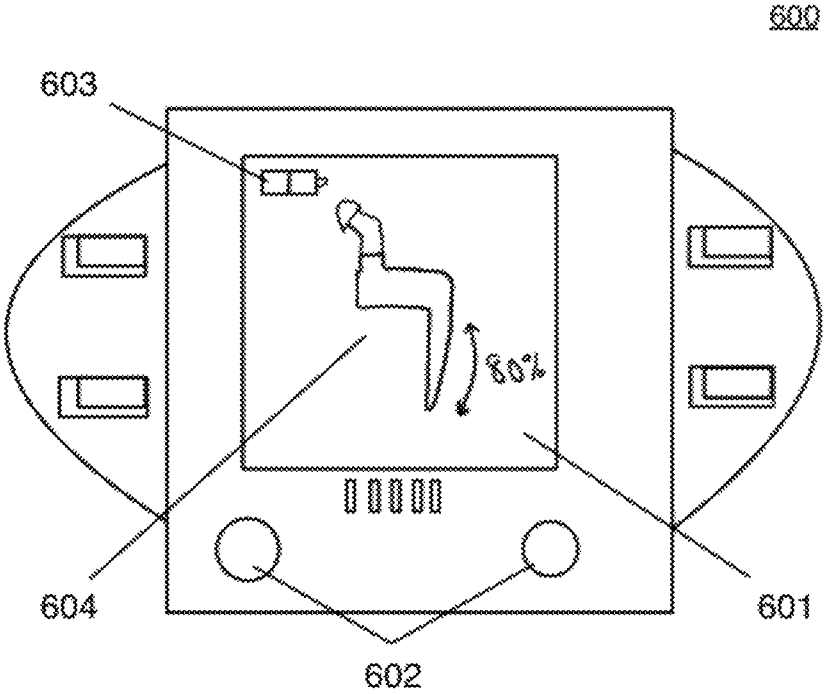
FIG. 13 is a perspective cross-section view of the external magnet device, showing two large and one small internal magnet.

The preferred treatment plan would vary per patient based on the determined need for length adjustment on a case-specific basis. The physician can program the device to be customized to patient needs. For example, if a patient is limited to 0.75 mm compression per day, the device will be programmed to not exceed over 0.75 mm within 24 hours. In one embodiment as shown in FIG. 13, the device contains an internal sensor which can monitor the number of rotations of the magnetic rod. The sensor can measure the number of rotations that the magnetic rod has undertaken. The internal sensor feedback algorithmically correlates, based on current industry standards, to a magnitude of displacement of the lengthening screw. The current treatment progress is shown in the screen 601. In other embodiments, there are sensors placed in the gearbox adjacent to the lengthening rod that can sense distension. These communicate back to the external device, which displays distension/lengthening rod location in space compared to the sensor on the display screen.

FIG. 16 describes the operating external magnetic device step 850. The external magnetic device is designed to be strapped to the lateral hip, adjacent to the greater trochanter, and therefore, the magnetic rod within the implant. To optimize ease of compression or lengthening, the patient will be in the supine position when using the device or in the lateral decubitus position, with the device on the hip furthest from the resting surface. This minimizes the force of gravity during modulation. In one embodiment, when the length modulating medical implant device is activated by pushing the button 602 on external magnetic device 600, a step motor located within the device turns the large magnets, which turns the implant magnetic rod 450.

Figure 14:
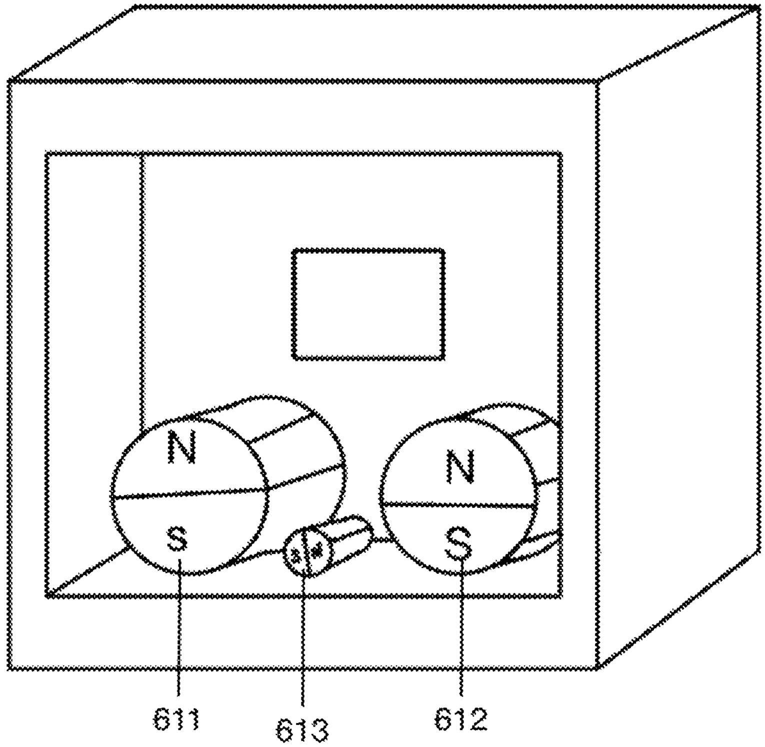
FIG. 14 is a schematic view of the magnetic poles from the two large and one small magnets within the external magnet device.
Figure 15:
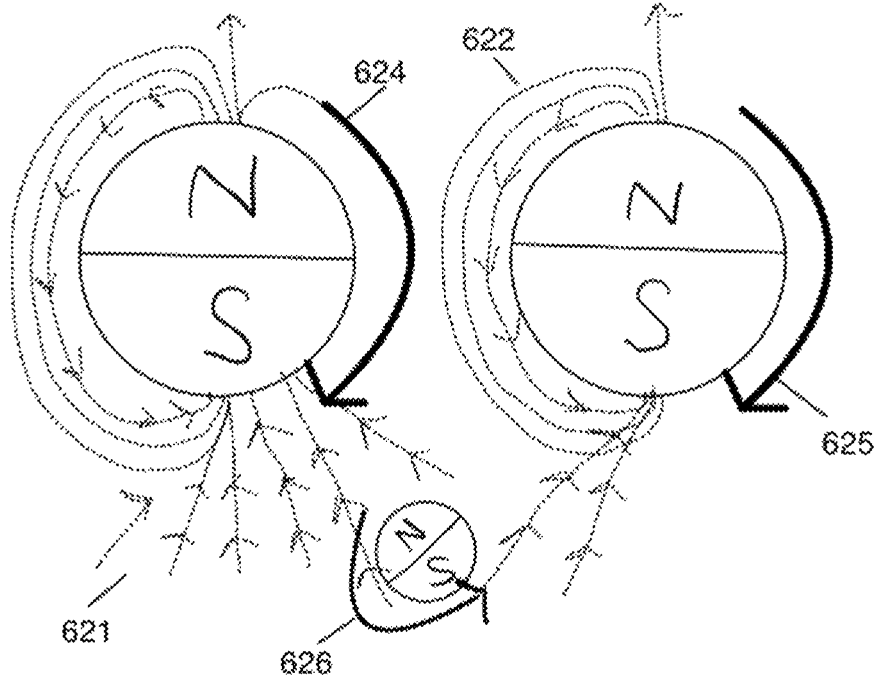
FIG. 15 illustrates how the external magnetic device operates.

FIG. 15 illustrates how the external magnetic device 600 (FIG. 13) operates. The magnetic field 622, 624 created by the external device causes rotation of the implant magnet. It is able, based on conventional programming, to turn the implant magnet both clockwise and counterclockwise. In another embodiment, when the length-modulating medical implant device is activated by pushing the button 602 on external magnetic device 600 (FIG. 13), a step motor located within the device turns the large magnets, which turns the smaller magnet 613 (FIG. 14), which communicates with the implant magnetic rod 450 (FIG. 6).

Within the device, there are sensors that communicate with sensors within the implant. These gather information on the rate of rotation of the magnetic rod, the torque of the rod, the distension progress of the lengthening screw, among other data. These may include Hall sensors but in other embodiments, laser, force, or pressure sensors may be utilized. At least one circuit board is housed in the external device for coordination of the display screen, sensors, and motor commands. A memory chip may also be placed in conjunction with the circuit board in order to store information such as time and duration of a length modulation session, total length change, and other analyses of the implant, potentially including malfunctions. In one embodiment, the lengthening procedure will be done in the physician's office. In other embodiments, the external magnetic device 600 (FIG. 13) may be brought to the patient's home to allow a patient or his/her care provider to start the lengthening procedure.

This device is a medical hip prosthesis purported to replace the acetabulofemoral joint, similar to a traditional total joint replacement implant, and simultaneously provide length modulation by post-operative manipulation of an external magnetic driver system. This external system is designed to allow anterograde and retrograde displacement of the femur. This prosthetic device can be non-surgically manipulated to displace the femur proximally or distally in order to correct the discrepancy in limb length. This lengthening process can occur over a period ranging from at least one day to the course of several weeks, since the extension or retraction of the implant must be done gradually to protect the health and integrity of surrounding tissues. In some embodiments, lengthening can occur in at least 0.20 mm increments, wherein the prosthesis is lengthened by at least one increment per session. Sessions may occur one to several times daily, depending on the lengthening requirements of the patient.

In other embodiments, lengthening may occur in increments less than 0.20 mm to for safety. Once a physician objectively determines the Limb Length Discrepancy, the patient can be provided with an external driver that magnetically communicates with the implant. The physician can first program the external device to distract at distinct intervals to optimize patient safety. The patient then can operate the device out of the office according to physician directions. The patient can follow-up with the physician at the physician's discretion to monitor progress of the length modulation. Once ideal anterograde or retrograde femoral displacement is achieved, the patient can return the external device to the physician and follow-up as required.

II. Shoulder Prosthesis

A length-modulating total joint prosthesis may be adapted for replacement of the shoulder joint and length-adjustment of the arm. The device may be a solution for post-operative lengthening of the arm after reverse total shoulder arthroplasty. The device is composed of a non-biodegradable medical grade metal or metal alloy such as cobalt-chrome or titanium, and may also be composed of ceramic or polyethylene. An embodiment of the invention configured for use as a shoulder prosthesis comprises an implant head and stem, wherein the stem is conical in shape. The stem tapers conically to a tip at the distal end and is flat at the proximal end. The flat portion of the stem mimics the anatomy of the joint socket and is attached to an articulating disc. The vertical axis of the stem is parallel to that of the humerus. In one embodiment, the length of the stem is one third that of the humerus. The implant ball is a half-sphere shape with a flat surface that faces the glenoid and a spherical surface that faces the joint socket. The flat side of the ball attaches to a plate that fixes the ball to the glenoid. Screws secure the ball and plate to the glenoid by entering the glenoid perpendicular to the articulative surface and ensure the stability of the implant.

A length-modulating shoulder prosthesis further comprises a lengthening mechanism contained within a housing in the proximal stem. The lengthening mechanism may alternatively include a rack-and-pinion system, hydraulics, manual screwdriver, planetary gear, fine threaded rod with interlocking gears, motor powered, battery powered, heat powered, magic mold injection, and spring-loading. In one embodiment, wherein a rack-and-pinion system comprises the lengthening mechanism, the number of rails is proportional to the size of the implant, which are available in various sizes and degrees depending on the dimensions of the patient's humerus and the patient's weight. The number of rails may range from four to six rails. The rails are contained in the housing in the proximal stem. A magnetic rod mechanically coupled to a series of gears is contained in a housing within the distal stem. The series of gears is mechanically coupled to the rack-and-pinion system of the proximal stem. In one embodiment, a gearbox containing the lengthening mechanism is inserted intraoperatively into the stem after the stem has been impacted into the intramedullary space of the humeral shaft to avoid gearbox damage.

The length-adjustable prosthesis further comprises an external lengthening device that contains at least one rotatable permanent magnet. After reverse total shoulder arthroplasty is complete, the external device is placed over the patient's skin in proximity to the implant. The magnetic field of the at least one rotatable magnet of the external device forces the rotation of the internal magnetic rod within the implant. Rotation of the magnetic rod activates the lengthening mechanism, wherein the rotation can occur in 1 mm increments. As the magnetic rod rotates, the lengthening portion can move proximally or distally to allow shortening or lengthening of the humerus.

We claim:

1. A length-adjustable total hip joint prosthesis, comprising:

a femoral prosthetic stem comprising a distal stem portion and a proximal stem portion, a rectangular housing disposed within the proximal stem portion, wherein the femoral prosthetic stem is configured for insertion into an intramedullary space of a femur, wherein the housing comprises:

a permanent magnetic rod configured for circumferential rotation, wherein the rod is rotationally coupled to an input gear, a first gear set comprising a first plurality of parallel spur gears, wherein the first gear set is operatively coupled to the input gear, a second gear set comprising a second plurality of parallel spur gears, wherein the first and the second gear sets intermesh in parallel, and a lengthening screw having a first portion disposed within the housing and rotationally coupled to an output gear and a second portion extending out of the housing; and an implant neck comprising a threaded internal cavity along a length thereof configured for receiving the second portion of the lengthening screw, wherein a proximal part of the implant neck is configured for coupling to an implant head, and the implant head is configured for insertion into an acetabulum, wherein the permanent magnetic rod and the lengthening screw are distinct and separate from one another, wherein rotation of the permanent magnetic rod in a first axial direction through a plurality of rotations causes the implant neck to move toward the housing to effect a decrease in a length of the prosthesis, and wherein rotation of the permanent magnetic rod in a second axial direction through a plurality of rotations causes the implant neck to move away from the housing to effect an increase in a length of the prosthesis.

2. The total hip joint prosthesis of claim 1, further comprising an external adjustment device comprising at least two rotatable permanent magnets.

3. The total hip joint prosthesis of claim 2, wherein operation of the external adjustment device over a patient's skin generates a magnetic force that causes rotation of the magnetic rod.

4. The total hip joint prosthesis of claim 1, further comprising a telescopic shaft, wherein the shaft houses the second portion of the lengthening screw and a distal part of the neck.

5. The total hip joint prosthesis of claim 4, wherein the neck is a hexagonal cylinder further comprising grooves, and wherein the telescopic shaft is a hexagonal cylinder further comprising an inward protrusions, such that the protrusions of the shaft fit into the grooves of the neck.

6. The total hip joint prosthesis of claim 1, wherein the lengthening screw is coupled for rotation within the neck by a bearing.

7. The total hip joint prosthesis of claim 1, wherein a gear ratio of the first and the second gear sets ranges from about 1:500 to 1:2000.

8. The total hip joint prosthesis of claim 1, wherein a lateral surface of the housing comprises a lateralized ledge.

9. The total hip joint prosthesis of claim 1, wherein the femoral prosthetic stem further comprises a porous coating.

* * * * *